United States Patent [19]

Benitez et al.

[11] 4,332,738
[45] Jun. 1, 1982

[54] ESTERIFICATION OF NEO ACIDS BY THE USE OF CATION EXCHANGE RESINS

[75] Inventors: Francisco M. Benitez; Michael F. English, both of Baton Rouge, La.

[73] Assignee: Exxon Research & Engineering Co., Florham Park, N.J.

[21] Appl. No.: 209,788

[22] Filed: Nov. 24, 1980

[51] Int. Cl.$^3$ ............................ C09F 5/08; C08H 3/00
[52] U.S. Cl. ................................. 260/410.6; 260/404; 260/404.5; 260/399; 260/410.9 R; 560/254; 560/250; 560/251; 560/252; 560/253; 560/264; 560/265
[58] Field of Search .......... 260/410.5, 410.6, 410.9 R, 260/410.9 D, 404, 404.5 R, 399; 560/263, 254, 250, 251, 252, 253, 264, 265

[56] References Cited

U.S. PATENT DOCUMENTS

| | | | |
|---|---|---|---|
| 2,936,315 | 5/1960 | Whitaker | 560/265 |
| 3,037,052 | 5/1962 | Bortnick | 260/485 |
| 3,349,107 | 10/1967 | Pawlenko et al. | 260/410.9 |
| 3,562,300 | 2/1971 | Chao et al. | 260/410.6 X |
| 3,579,548 | 5/1971 | Whyte | 260/410.7 |
| 3,590,073 | 6/1971 | Carr et al. | 260/410.9 D |
| 3,694,382 | 9/1972 | Kleiman et al. | 260/410.6 X |
| 4,125,549 | 11/1978 | Coopersmith | 260/425 |

FOREIGN PATENT DOCUMENTS 960011 9/1961 United Kingdom .
998974 4/1963 United Kingdom .

OTHER PUBLICATIONS

A Paper by Coopersmith et al. entitled "Preparation of Hydrolytic Stability of Trialkylacetic Acid Esters", I&EC, 5, No. 1, pp. 46–79, (Mar. 1966).

*Primary Examiner*—John F. Niebling
*Attorney, Agent, or Firm*—Roland A. Dexter

[57] ABSTRACT

The esterification of neo acids catalyzed by the presence of a macro-reticular structured sulfonic acid cation exchange resin proceeds under mild conditions with a wide variety of alcohols to give readily recoverable esters in high yields and high purity and an easily recoverable and reusable catalyst.

5 Claims, No Drawings

ESTERIFICATION OF NEO ACIDS BY THE USE OF CATION EXCHANGE RESINS

FIELD OF THE INVENTION

The invention relates to the esterification of a neo acid with an alcohol in the presence of a cation exchange resin and more particularly, to the esterification of neo acid having from 5 to 28 carbon atoms with an alcohol including a polyol having from 2 to about 100 carbon atoms in the presence of a macro-reticular sulfonic acid cation exchange resin.

BACKGROUND OF THE INVENTION

The carbonylation of olefins at high temperatures and pressures produces after hydrolysis of the acid-catalyst complex, organic acids of a heavily branched nature, i.e., neo acids, which are totally substituted at the α-carbon and also known as trialkyl acetic acids. The difficulty associated with the preparation of esters of neo acids is well known as is the property of enhanced hydrolytic stability of these esters once prepared. The difficulty in preparation and the enhanced hydrolytic stability of these neo acid esters may, in theory, be attributed to either a steric or an ionization effect. It appears that the rate of esterification decreases sharply as the degree of acid chain branching increases. A paper by Coopersmith et al entitled "Preparation of Hydrolytic Stability of Trialkylacetic Acid Esters", I&EC, 5, No. 1, pp. 46–49 (March 1966) reports that on a laboratory basis, esters of neo-acids can be produced in high yields with a homogeneous acid catalyst (p-toluene sulfonic acid, sulfuric acid) and a water entrainer. However, the reported heterogeneous sulfonic acid polymer catalyst (Amberlyst IR120H, sold by Rohm & Haas, Philadelphia, Pa., provoked a very poor yield of neo acid ester.

Coopersmith et al in U.S. Pat. No. 4,125,549 teach an improvement in the preparation of a neo decanoic acid ester (isooctyl neodecanoate) in the presence of a heterogeneous sulfonic acid catalyst by steam stripping the distilled ester product until the sulfur content is less than 20 ppm and in the presence of an oxidant. The above-taught process required extensive purification procedures to avoid the contamination inherent with the homogeneous sulfonic acid catalyst.

In a more difficult esterification reaction of neo acids than that of Coopersmith et al, Whyte (in U.S. Pat. No. 3,579,548) teaches the preparation of glycerol esters in the presence of both toluene sulfonic acid (Examples I, II and IV) and sulfuric acid (Example III); however, complex purification and/or separation procedures for separation of said ester from the homogeneous catalyst are required.

Finally, U.S. Pat. No. 3,590,073 teaches the use of macro-reticular sulfonic acid cationic exchange resins for catalysis of the esterification of tertiary alcohols with organic carboxylic acids having from 2 to 20 carbon atoms with relatively low yields. With sterically hindered alcohols, the presence of a heterogeneous sulfonic acid type cationic exchange resin appears to inhibit the usual tendency of said alcohols to dehydrate and produce an olefin which subsequently polymerizes in the presence of an acid catalyst, i.e. an undesirable reaction competing with esterification but not one of relevance for the esterification of trialkylacetic acid.

It is an object of this invention to overcome the foregoing disadvantages and/or teachings of the prior art.

It is a further object of this invention to provide an improved method for the esterification of neo-acids in high yield and high purity.

SUMMARY OF THE INVENTION

In accordance with the objects of this invention, it has been discovered that surprisingly excellent yields are possible in the direct esterification of an aliphatic acyclic acid having from 5 to 28 carbon atoms in the molecule when said acid is reacted with an alcohol in a non-aqueous system in the presence of a sulfonic acid cation exchange resin used in its acid form and having a macro-reticular structure.

The new process claimed herein allows the synthesis of neo acid (preferably neo pentanoic acid and neo decanoic acid) esters to proceed in high yields at temperatures between 50° C. and 170° C. by mixing the desired neo acid stoichiometrically with the alcohol in the presence of a catalytic amount, preferably about 10 percent by weight, based on the total weight of reagents, macro-reticular sulfonic acid cationic resin and an inert solvent used to azeotrope the water formed in the reaction. Purification of the neo acid ester can be maintained at a minimum because of the ease of the catalyst separation and the lack of reaction by-products.

DETAILED DESCRIPTION OF THE PREFERRED EMBODIMENTS OF THE INVENTION

Acid Reactants

The difficult esterifiable neo acids or fully substituted α-branched carboxylic acids having from 5 to 28 carbon atoms can be alternatively expressed according to Formula I hereafter:

(FORMULA I)

wherein $R_1$, $R$ and $R_3$ are each selected from alkyl groups of 1 to 24 carbons and the total carbons in $(R_1+R_2+R_3)$ being from 3 to 26. These α-branched chain carboxylic acids of Formula I are commercially available materials and are commonly referred to as neo acids, synthetic trialkylacetic acids, or tertiary carboxylic acids (see The Journal of the American Oil Chemists Society, 45, No. 1, January 1968, pages 5–10). These neo acids can be prepared by the well known Kock process from olefins, carbon monoxide and water as described by H. Koch in Brennstaff Chem. 36, 321 (1955). Further details on methods for making α-branched carboxylic acids useful herein as Formula I compounds are found in British Pat. Nos. 960,001 and 998,974, and U.S. Pat. No. 3,349,107, all incorporated herein by reference.

Preferred neo acids within the scope of this invention are those wherein $R_1$, $R_2$ and $R_3$ are each selected from alkyl groups of from 1 to 26 carbon atoms, and the total carbon atoms in $R_1+R_2+R_3$ is from 3 to 20.

Neo acids are often made from olefin feedstocks which are random isomeric mixtures in regard to the position of the olefinic bond. These acids are thus random isomeric mixtures of neo acids.

Alcohol Reactants

1. Monohydric alcohols

Useful monohydric alcohols can be characterized by the formula R'OH wherein R' is a hydrocarbyl group containing from 1 to 24, preferably 1 to 12, carbons such as methyl, ethyl, propyl, butyl, hexyl, octyl, decyl, lauryl, stearyl, phenyl, nonylphenyl and mixtures thereof; or, an alkyl group containing a heteroatom and represented by radicals such as $CH_3O(CH_2CH_2O)_nCH_2CH_2-$, $CH_3S(CH_2CH_2S)_nCH_2CH_2-$, $(CH_3)_2N(CH_2CH_2NCH_3)_nCH_2CH_2-$; etc. where n = 1–10, and 1-aza-3,7-dioxabicyclo (3.3.0)oct-5-methanol.

2. Polyhydric alcohols

The polyhydric alcohols used in esterifying the neo acids can have a total of 2 to about 100 carbon atoms and can be represented by the formula:

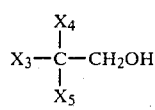

wherein: $X_3$ is hydrogen, $C_1$ to $C_5$ alkyl, hydroxyl, hydroxyalkyl $HO(CH_2)_n$ wherein n is 1–10, hydroxyalkoxy $HO(CH_2CH_2O)_n-$, wherein n is 1–40, hydroxyalkylthio $HOCH_2CH_2S(CH_2CH_2S)_n-$, wherein n is 1 to 10; and hydroxyalkylamino $HO(CH_2CH_2NCH_3)_n-$, wherein n is 1 to 10; and $X_4$ and $X_5$ may be the same or different and represent hydrogen, $C_1$ to $C_5$ alkyl and $C_1$ to $C_5$ hydroxyalkyl groups and their ester, ether, acetal or ketal derivatives. Examples of useful acetals and ketals include mono and bis-formals of pentaerythritol; mono and bis-acetal and benzal analogs of pentaerythritol; and the cyclic, formal and acetal of $HO(CH_2CH_2O)_nH$ wherein n is 4–8.

3. Esterification Catalyst

The catalysts used are the sulfonic acid type cation exchange resins having a macro-reticular structure. As the name implies, these are used in their acid or hydrogen form. These catalysts, their properties and method of preparation are shown in U.S. Pat. No. 3,037,052. These are available commercially and are sold under the trade name Amberlyst-15 by Rohm & Haas of Philadelphia, Pa. These macro-reticular structure catalysts have been found to be unexpectedly superior to micro-reticular prior art sulfonic acid type cation exchange resins as illustrated by Amberlyst IR120H referenced earlier.

The percent of catalyst to total reactants to be esterified according to this invention ranges on a weight basis from 5 to 15, preferred to 8 to 12, optimally about 10.

4. Esterification Process

Typically, the esterification method is carried out by adding about one mole of alcohol, preferably monool, per mole of neo acid, with or without an inert diluent, in the presence of the macro-reticular sulfonic acid esterification catalyst, and heating the mixture at 50°–170° C., preferably 100° to 150° C., until the reaction is complete by infrared analysis of the product as indicated by maximal absorptions for ester functionality.

The higher temperatures are only necessary when the higher alcohols and acids are used. In general, high temperatures should be avoided to avoid catalyst degradation and this can be accomplished by the use of non-aqueous and non-reactive solvents well-known in the art, for example, toluene.

The reaction is carried out in a non-aqueous system, the reactants and catalyst being substantially anhydrous. The reaction can be carried out either in batch or continuous manner as a continuously stirred tank reactor. In the continuous method, alternatively, the reactants are passed over a bed of the cation exchange resin, for example, in a tubular reactor which can be temperature controlled. In the batch process, the reactants and product are separated from the resin by filtration or centrifugation and the reactants and product are separated by conventional methods. The resin catalyst can be reused for subsequent esterification, a property not available from a homogeneous catalyst. The following examples are provided for the purpose of illustrating the invention in greater detail, but these are not to be construed as limiting.

EXAMPLES 1–10

The illustrative syntheses of neo pentanoic acid esters and neo decanoic acid esters were carried out in batch reactions utilizing an equimolar mixture of the neo acid and the alcohol with 10 percent by weight of Amberlyst-15, a commercial macro-reticular sulfonic acid cation exchange resin in which the resin is believed to be poly styrene and sold by Rohm & Haas Co. of Philadelphia, Pa. based upon the weight of the neo acids and 150 ml. of toluene. The subsequent Table I and II show the temperature and time conditions along with the yield of the respective ester.

TABLE I

Syntheses of Neo Pentanoic Acid Esters[1]

| Examples | Acid/Alcohol | % Yield of Ester[2] | Temperature of Reactuib, °C. | Hours Required to Collect $H_2O$[3] |
|---|---|---|---|---|
| 1 | $C_5$Neo[5]/$C_{10}$Oxo[6] | 97.5 | 124 | 3 |
| 2 | $C_5$Neo/$C_{13}$Oxo[6] | 96.5 | 126 | 3 |
| 3 | $C_5$Neo/Phenol | 96.6 | 119 | 8 |
| 4 | $C_5$Neo/TMP[4] | 95.2 | 140 | 43 |

[1] All are batch reactions. All reactions carried out as a stoichiometric mixture of the neo acid and the alcohol containing 10 percent by weight based on the weight of the reagents, Amberlyst 15 and 150 ml. of toluene.
[2] Percent yield calculated on purified, isolated product.
[3] Time shown is the hours required to collect the theoretical maximum amount of water.
[4] TMP = trimethylol-propane or 2-ethyl-2-(hydroxymethyl)-1, 3-propanediol.
[5] Neo pentanoic (prime grade) acid sold by Exxon Chemical Americas, Houston, Texas.
[6] The Oxo alcohols are sold as Oxo Decanol and Oxo Tridecanol, respectively, by Exxon Chemical Americas, Houston, Texas.

TABLE II

Syntheses of Neo Decanoic Acid Esters[1]

| Examples | Acid/Alcohol | % Yield of Ester[8] | Temperature of Reaction, °C. | Hours Required to Collect $H_2O$[9] |
|---|---|---|---|---|
| 5 | $C_{10}$/Neo[10] $C_{10}$Oxo | 96.1 | 127 | 4.5 |
| 6 | $C_{10}$Neo/$C_{13}$Oxo | 93.4 | 129 | 4.5 |
| 7 | $C_{10}$Neo/$C_{12}$linear | 97.9 | 148 | 2.1 |
| 8 | $C_{10}$Neo/Phenol | 89.7 | 123 | 6.0 |
| 9 | $C_{10}$ Neo/Ethylene Glycol | 83.0 | 140 | 15.0 |
| 10 | $C_{10}$ Neo/Nonyl | 82.5 | 142 | 9.0 |

TABLE II-continued

Syntheses of Neo Decanoic Acid Esters[1]

| Examples | Acid/Alcohol Phenyl | % Yield of Ester[8] | Temperature of Reaction, °C. | Hours Required to Collect $H_2O$[9] |
|---|---|---|---|---|

[1]See Table I
[8]Percent yield calculated on purified, isolated product.
[9]Time required to collect the theoretical maximum amount of water.
[10]Neo decanoic acid (Technical Grade) sold by Exxon Chemical Americas, Houston, Texas.

Neo decanoic acid (prime grade) contains 95.2 percent of $C_{10}$, 1.2 percent of $C_6$, $C_8$ 2.3% $C_9$ and 0.9 percent of $C_{11}$–$C_{17}$ trialkylacetic acids whereas Neo decanoic acid (Technical Grade) contains 82.7 weight percent of $C_{10}$, 5.1 weight percent of $C_6$–$C_9$, 0.7 percent of $C_{11}$–$C_{17}$ and 7.3 percent of $C_{28}$ and higher carbons in the trialkylacetic acid. The above data shows that the rate of esterification of neo decanoic acid as in the case of the neo pentanoic acid with straight chain alcohols is faster than oxo alcohols, followed by the aromatic alcohols and the polyols are the most difficult to esterify. It is also noted that the reactions should be kept essentially free from water by its removal during the esterification since the cationic exchange resin will tend to deteriorate if it is kept in contact with moistures at temperatures higher than about 150° C.

These products are believed to have excellent hydrolytic stability and/or improved low temperature performance properties not possessed in as an improved degree by other neo acid esters which can be prepared by the process of the invention disclosed herein.

The products of Examples 1, 2, 3, 5 and 6 represent $C_5$–$C_{28}$ neo acid esters of an alcohol of the class consisting of $C_{10}$ to $C_{100}$ monohydroxy alkanols and $C_6$ to $C_{24}$ monohydroxy aryl alcohols having utility as lubricants, lubricating oil pour point depressants and as wax crystal modifiers for lubricating oils.

EXAMPLE 11

In the discussion leading up to the Examples, it is taught that the process of the invention provides esterification of difficulty esterifiable branched acids under relatively mild conditions and at high yields. The following data of Table III shows the water evolution from the esterification measured against time of the esterification reaction for a $C_{13}$ Oxo alcohol with Neo pentanoic acid (prime grade) under reaction conditions which are relatively mild and expedient. The esterification was carried out with a stoichiometric amount of neo pentanoic acid and $C_{13}$ Oxo alcohol dissolved in toluene and carried out at the azeotropic boiling point of toluene and water.

TABLE III

Water Evolution Vs. Time

| Time, Minutes | mL of $H_2O$ for $C_5$ Neo/$C_{13}$Oxo | mL of $H_2O$ for $C_{10}$ Neo/$C_{13}$Oxo |
|---|---|---|
| 0 | 0.0 | 0.0 |
| 15 | 1.4 | 1.0 |
| 30 | 2.7 | 2.1 |
| 45 | 4.1 | 3.1 |
| 60 | 5.5 | 4.2 |
| 75 | 6.9 | 5.2 |
| 90 | 7.7 | 6.3 |
| 105 | 8.5 | 7.3 |
| 120 | 9.0(*) | 8.4 |
| 129 | — | 9.0(*) |

(*)Maximum theoretical water yield

This invention in its broader aspect is not limited to the specific details shown and described and departures may be made from such details without departing from the principles of the invention and without sacrificing its chief advantages.

What is claimed is:

1. A method for the direct esterification of a neo acid having from 5 to 28 carbon atoms in its molecule which comprises contacting said acid with an alcohol in a non-aqueous system in the presence of a sulfonic acid cation exchange resin used in its acid form and having a macro-reticular structure.

2. The method according to claim 1 wherein the esterification reaction is carried out at a temperature of about 50° C. to 170° C.

3. The method according to claim 1 wherein the mole ratio of said neo acid to said alcohol is substantially stoichiometric.

4. The method according to claim 3 wherein said acid is neo pentanoic acid.

5. The method according to claim 3 wherein said acid is neo decanoic acid.

* * * * *